US011642090B2

(12) United States Patent
Cohen et al.

(10) Patent No.: US 11,642,090 B2
(45) Date of Patent: May 9, 2023

(54) CARDIAC ELECTRICAL MAPPING AND ABLATION

(71) Applicant: Sirona Medical Technologies, Inc., Andover, MA (US)

(72) Inventors: Richard Jonathan Cohen, Newton, MA (US); Ali Haghighi-Mood, Andover, MA (US)

(73) Assignee: Sirona Medical Technologies, Inc., Andover, MA (US)

( * ) Notice: Subject to any disclaimer, the term of this patent is extended or adjusted under 35 U.S.C. 154(b) by 399 days.

(21) Appl. No.: 16/887,258

(22) Filed: May 29, 2020

(65) Prior Publication Data

US 2020/0375555 A1    Dec. 3, 2020

Related U.S. Application Data

(60) Provisional application No. 62/854,176, filed on May 29, 2019.

(51) Int. Cl.
*A61B 6/12* (2006.01)
*A61B 5/00* (2006.01)
(Continued)

(52) U.S. Cl.
CPC ............... *A61B 6/12* (2013.01); *A61B 5/287* (2021.01); *A61B 5/333* (2021.01); *A61B 5/339* (2021.01);
(Continued)

(58) Field of Classification Search
CPC ........... A61B 6/12; A61B 6/032; A61B 6/487; A61B 6/503; A61B 5/287; A61B 5/333; A61B 5/339; A61B 5/363; A61B 5/6859; A61B 5/367; A61B 18/1492; A61B 990/39; A61B 2018/00351; A61B 2018/00577; A61B 2018/00613; A61B 2018/002; A61B 2018/00178; A61B 2018/00196;
(Continued)

(56) References Cited

U.S. PATENT DOCUMENTS

| 4,940,064 A | 7/1990 | Desai |
| 5,215,103 A | 6/1993 | Desai |

(Continued)

FOREIGN PATENT DOCUMENTS

WO    2020243389 A1    12/2020

OTHER PUBLICATIONS

Wittkampf et al. (2012) "Myocardial Lesion Depth with Circular Electroporation Ablation Circulation", Arrhythmia and Electrophysiology, 5(3):581-586.
(Continued)

*Primary Examiner* — Peter Luong
(74) *Attorney, Agent, or Firm* — Mintz Levin Cohn Ferris Glovsky and Popeo, P.C.

(57) ABSTRACT

Improved mapping and ablation procedures and corresponding devices are provided. A variety of methods and apparatuses can be used for the treatment of cardiac arrhythmias by identifying the location of an arrhythmia source and ablating that source. The methods and apparatuses can provide an improved means of electrical mapping of the heart to identify the location of the arrhythmia source and advancing an ablation electrode to that location so that it may be ablated.

25 Claims, 8 Drawing Sheets

Method to Locate and Ablate a Source of Cardiac Arrhythmia
(when X-ray is used as Imaging Modality)

1. Introduce into the body a catheter containing on its distal end a plurality of electrodes one of which is used to deliver ablative energy (ablation electrode)
2. Position the catheter so that some or all of the electrodes are in contact with cardiovascular tissue
3. Obtain an X-ray image
4. Determine the locations of some or all of the electrodes on the X-ray image
5. If necessary induce the arrhythmia
6. Record electrical activity signals sensed by the electrodes
7. If necessary terminate the arrhythmia
8. Process the recorded signals to determine the relative times of arrival at each of the electrodes of an electrical impulse emanating from the arrhythmia source
9. Implement the Arrhythmia Source Localization procedure to compute the location of the arrhythmia source on the X-ray image, the conduction velocity, and the distance of the ablation electrode to the arrhythmia source
10. Display the location of the arrhythmia source on the X-ray image
11. If the computed distance of ablation electrode to arrhythmia source is less than a threshold value go to Step 14
12. Under X-ray guidance move the catheter so the ablation electrode is in close proximity to the arrhythmia source on the X-ray image
13. Go to Step 4
14. Deliver ablative energy to the arrhythmia source through the ablation electrode

(51) Int. Cl.
    *A61B 18/14* (2006.01)
    *A61B 90/00* (2016.01)
    *A61B 5/287* (2021.01)
    *A61B 5/333* (2021.01)
    *A61B 5/339* (2021.01)
    *A61B 5/363* (2021.01)
    *A61B 18/00* (2006.01)

(52) U.S. Cl.
    CPC ............ *A61B 5/363* (2021.01); *A61B 5/6859* (2013.01); *A61B 18/1492* (2013.01); *A61B 90/39* (2016.02); *A61B 2018/00351* (2013.01); *A61B 2018/00577* (2013.01); *A61B 2018/00613* (2013.01); *A61B 2090/3912* (2016.02); *A61B 2090/3966* (2016.02); *A61B 2218/002* (2013.01)

(58) Field of Classification Search
    CPC ........... A61B 2018/00702; A61B 2018/00875; A61B 2018/00267; A61B 2018/00357; A61B 2018/00363; A61B 2018/00642; A61B 2018/00821; A61B 2018/00839; A61B 2090/3912; A61B 2090/3966; A61B 2090/376; A61B 2218/002; A61B 2034/104; A61B 2017/00053; A61B 2576/00
    See application file for complete search history.

(56) References Cited

U.S. PATENT DOCUMENTS

| | | |
|---|---|---|
| 5,231,995 A | 8/1993 | Desai |
| 5,365,926 A | 11/1994 | Desai |
| 5,383,917 A | 1/1995 | Desai et al. |
| 5,397,339 A | 3/1995 | Desai |
| 5,433,198 A | 7/1995 | Desai |
| 5,500,011 A | 3/1996 | Desai |
| 5,620,481 A | 4/1997 | Desai et al. |
| 5,657,755 A | 8/1997 | Desai |
| 5,693,078 A | 12/1997 | Desai et al. |
| 5,857,464 A | 1/1999 | Desai |
| 6,052,612 A | 4/2000 | Desai |
| 6,308,093 B1 | 10/2001 | Armoundas et al. |
| 6,370,412 B1 | 4/2002 | Armoundas et al. |
| 6,522,905 B2 | 2/2003 | Desai |
| 6,574,492 B1 * | 6/2003 | Ben-Haim ........... A61B 5/6843 600/374 |
| 6,701,180 B1 | 3/2004 | Desai |
| 6,738,673 B2 | 5/2004 | Desai |
| 7,151,964 B2 | 12/2006 | Desai et al. |
| 8,050,732 B2 | 11/2011 | Desai |
| 8,457,721 B2 | 6/2013 | Desai |
| 8,882,761 B2 | 11/2014 | Desai |
| 9,717,558 B2 | 8/2017 | Desai |
| 10,709,499 B2 | 7/2020 | Desai |
| 10,709,501 B2 | 7/2020 | Desai |
| 2008/0071264 A1 | 3/2008 | Azure |
| 2008/0306394 A1 | 12/2008 | Zdeblick et al. |
| 2010/0023004 A1 | 1/2010 | Francischelli et al. |
| 2012/0184865 A1 * | 7/2012 | Harlev ................... A61B 18/00 600/509 |
| 2015/0126840 A1 | 5/2015 | Thakur et al. |
| 2015/0196217 A1 | 7/2015 | Harlev et al. |
| 2017/0319274 A1 | 11/2017 | Desai |
| 2018/0318013 A1 | 11/2018 | Mangual-soto et al. |
| 2019/0090942 A1 | 3/2019 | Haghighi-mood et al. |

OTHER PUBLICATIONS

Reddy et al. (2019) "Pulsed Field Ablation for Pulmonary Vein Isolation in Atrial Fibrillation", Journal of the American College of Cardiology, 74(3):315-326.

Packer et al. (2019) "Effect of Catheter Ablation vs Antiarrhythmic Drug Therapy on Mortality, Stroke, Bleeding, and Cardiac Arrest Among Patients With Atrial Fibrillation", JAMA, 321 (13):1261-1274.

Liang et al. (2015) "Long-term Outcomes of Ventricular Tachycardia Ablation in Different Types of Structural Heart Disease", Arrhythmia & Electrophysiology Review, 4(3):177-183.

* cited by examiner

FIG. 1

Method to Locate and Ablate a Source of Cardiac Arrhythmia (when X-ray is used as Imaging Modality)

1. Introduce into the body a catheter containing on its distal end a plurality of electrodes one of which is used to deliver ablative energy (ablation electrode)
2. Position the catheter so that some or all of the electrodes are in contact with cardiovascular tissue
3. Obtain an X-ray image
4. Determine the locations of some or all of the electrodes on the X-ray image
5. If necessary induce the arrhythmia
6. Record electrical activity signals sensed by the electrodes
7. If necessary terminate the arrhythmia
8. Process the recorded signals to determine the relative times of arrival at each of the electrodes of an electrical impulse emanating from the arrhythmia source
9. Implement the Arrhythmia Source Localization procedure to compute the location of the arrhythmia source on the X-ray image, the conduction velocity, and the distance of the ablation electrode to the arrhythmia source
10. Display the location of the arrhythmia source on the X-ray image
11. If the computed distance of ablation electrode to arrhythmia source is less than a threshold value go to Step 14
12. Under X-ray guidance move the catheter so the ablation electrode is in close proximity to the arrhythmia source on the X-ray image
13. Go to Step 4
14. Deliver ablative energy to the arrhythmia source through the ablation electrode

FIG. 2

Arrhythmia Source Localization Procedure (when X-ray is used as Imaging Modality)

1. Input the measured coordinates of the locations of the electrodes on the 2D X-ray image.
2. Input the times of arrival at each of the electrodes of an electrical impulse emanating from the arrhythmia source.
3. Compute the position and angular orientation of a simulated model of the electrode array such that the projection of the locations of the model's electrodes on the X-ray image are consistent with the measured locations of the electrodes on the X-ray image. As part of this computation, procedure also determines the value of a projection scale factor.
4. Compute the orientation of the tissue plane on which the electrodes lie.
5. Compute the locations of the electrodes on the tissue plane.
6. Search over the tissue plane to determine the location of an arrhythmia source on the tissue plane which is consistent with the locations of the electrodes on the tissue plane and the arrival times assuming a constant conduction velocity of the impulse along the plane.
7. Compute the value of the conduction velocity.
8. Compute the distance of the arrhythmia source from an ablation electrode in the array.
9. From the location of the arrhythmia source on the tissue plane compute the projected location of the arrhythmia source on the X-ray image.
10. Output the computed location of the arrhythmia source on the X-ray image, the computed conduction velocity, and the computed distance of the ablation electrode to the arrhythmia source.

CARDIAC ELECTRICAL MAPPING AND ABLATION

This application claims the benefit of priority to U.S. Provisional App. No. 62/854,176 of Cohen et al., filed on May 29, 2019 and entitled "Cardiac Electrical Mapping and Ablation," which is incorporated herein by reference in its entirety.

FIELD

Methods and devices are provided for electrical mapping and ablation of cardiac tissue.

BACKGROUND

Disorders of the electrical functioning of the heart can cause morbidity and mortality. These disorders are generally termed arrhythmias, commonly caused by disorders of impulse formation such as abnormal automaticity of the heart's normal pacemaker and/or disorders of impulse conduction such as partial or complete block of the electrical impulse.

There are various treatments for heart rhythm disturbances, such as with tissue ablation. However, there are many problems and limitations of the currently available methods and devices used for this procedure, such as inaccurately and precisely choosing a site of ablation.

Accordingly, there remains a need for improved mapping and ablation procedures.

SUMMARY

In general, improved mapping and ablation procedures and corresponding devices are provided.

Provided herein are methods and apparatuses for the treatment of cardiac arrhythmias by identifying the location of an arrhythmia source and ablating that source. The methods and apparatuses can provide an improved means of electrical mapping of the heart to identify the location of the arrhythmia source and advancing an ablation electrode to that location so that it may be ablated. The methods and apparatuses can also provide a more rapid means of treating cardiac arrhythmias and greatly reduces the cost and complexity of the procedure. Furthermore, the methods and apparatuses can be practiced with a single catheter used for both mapping and ablation, further reducing the cost and complexity of the procedure.

In one embodiment of a method to locate and ablate the source of an arrhythmia, a catheter containing an array of electrodes is introduced into the body. At least one of the electrodes must be capable of delivering ablative energy to biological tissue. In one embodiment, the catheter is introduced into the cardiovascular system through an artery or a vein and is placed inside one of the cardiac chambers to access the inner (endocardial) surface of the heart. In another embodiment, the catheter may be introduced through the chest wall to access the outer (epicardial) surface of the heart.

In one embodiment, deployable wings of a catheter contain radio-dense markers that can be seen on an X-ray and enable an operator to determine which electrode is which. In one embodiment, an apparatus also includes an element to amplify and filter the electrical signals recorded from a catheter's electrodes and an element to convert the resulting analog signals to digital signals that may be imported into a computer.

In addition, the apparatus can include an energy source for ablating biological tissue. In one embodiment, the ablation energy source may generate radiofrequency electrical energy. In another embodiment, the ablation energy source may generate electrical energy configured to irreversibly electroporate biological tissue. The energy source in addition to delivering ablative energy to one or more ablation electrodes through the catheter, may also receive signals from the catheter that are in turn used to control the delivery of ablative energy back to the catheter. Such signals may include the temperature of one or more ablation electrodes and the electrical impedance of one or more electrodes.

In one embodiment, the method can be applied to identify the location of an arrhythmia source but not to ablate it. In this embodiment, none of the electrodes on the electrode array need to be configured to be able to deliver ablative energy to biological tissue.

In one embodiment, the depth of the arrhythmia source in the cardiovascular tissue is computed from the locations of the electrodes in the X-ray plane and the arrival times at the electrodes of the electrical impulse emanating from the arrhythmia source.

In another embodiment, the one or more ablation electrodes are irrigated with an irrigation fluid delivered through a tube in the shaft of the catheter during the ablation procedure.

In another embodiment, the conduction velocity of the electrical impulse is not assumed to be constant in all directions but may be represented by a two-component spatial vector. In another embodiment, the recordings obtained from the electrodes are processed to obtain other electrical measures in addition to the electrical measure of the arrival times of the electrical impulse emanating from the arrhythmia source. In another embodiment, electroanatomic imaging can be employed in addition to, or in replacement of, X-ray imaging.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

This invention will be more fully understood from the following detailed description taken in conjunction with the accompanying drawings.

FIG. 1 is a flow chart of a method to locate and ablate a source of cardiac arrhythmia.

FIG. 2 is a flow chart of the arrhythmia source localization procedure.

DETAILED DESCRIPTION

Figure 3:
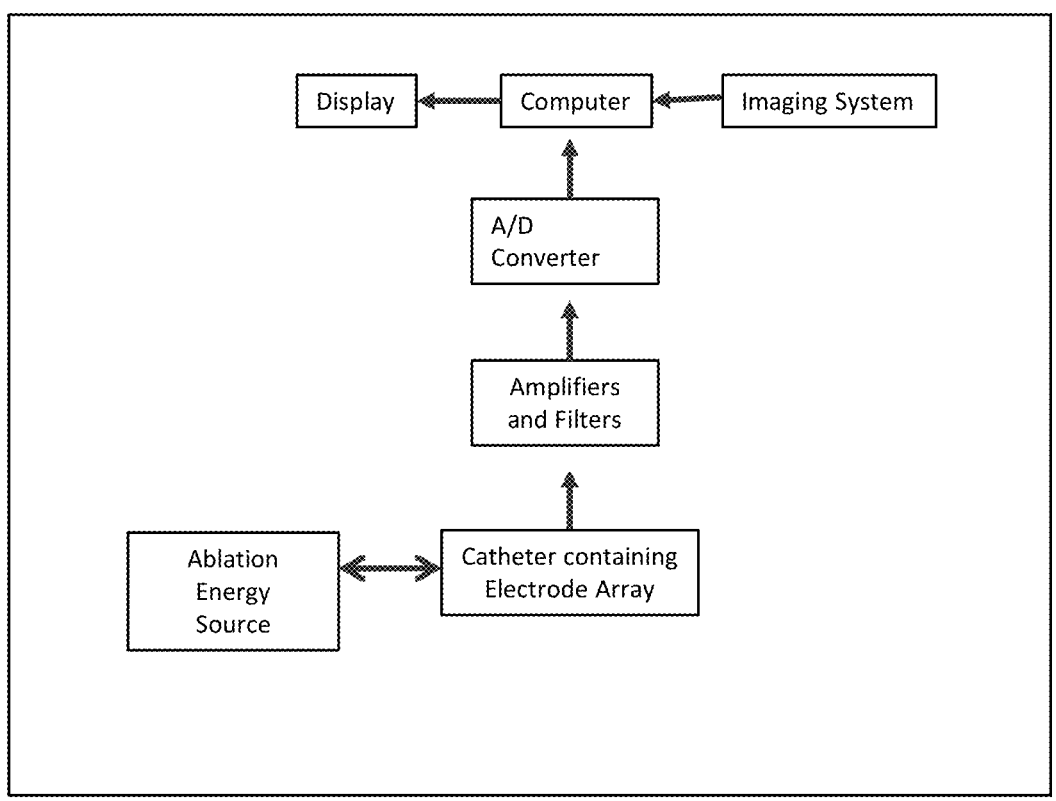
FIG. 3 is a block diagram of the apparatus for improved cardiac electrical mapping and ablation

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used. Like reference symbols in the various drawings indicate like elements.

Human life depends on the effective functioning of the heart on a second to second basis. If the heart ceases functioning for greater than about four minutes brain death ensues. The pumping function of the heart enables the blood to release carbon dioxide and pick up oxygen in the lungs. The oxygen, along with nutrients, hormones and other needed chemical species are delivered via the circulation to the body's tissues and waste products are removed and eliminated via the kidney and other mechanisms.

The heart can be thought of as an electromechanical four chamber pump. The right and left atria serve as booster pumps that aid in the filling of the heart's main pumping chambers—the right and left ventricles. Venous blood from the body returns through the vena cava to the right atrium. From the right atrium the blood passes into the right ventricle. The right ventricle pumps blood via the pulmonary artery through the lungs. The blood then returns from the lungs through the pulmonary veins that empty into the left atrium. From the left atrium the blood flows into the left ventricle which then pumps the blood via the aorta into the systemic circulation and then returns to the right atrium through the vena cava thus completing the circuit. Each of the ventricles have inlet and outlet valves to enable the filling of the ventricular chambers when the ventricles are relaxed (diastole) and to ensure the blood is pumped in the forward direction when the ventricles contract (systole).

The mechanical contraction of cardiac muscle is controlled by the propagation of an electrical impulse. The electrical impulse propagates through the heart muscle and initiates the contraction of the muscle. Cardiac muscle cells in the sino-atrial node are specialized to automatically initiate the electrical impulse on a regular basis (normally at a rate of 60 to 100 beats per minute) and thereby serve as the heart's normal pacemaker. Other specialized muscle cells in the atrio-ventricular-node serve to delay conduction of the electrical impulse between the heart's atria and the heart's ventricles. This delay of about 0.1 seconds allows the atria time to contract to aid in the filling of the ventricles before the ventricles begin to contract. Other specialized cells in the ventricles form the His-Purkinje system that serves as a high-speed cabling system that rapidly distributes the electrical impulse to the different regions of the ventricles so that the ventricles contract in a synchronous fashion thereby enhancing their ability to function effectively as pumps. If the His-Purkinje system is not functioning for some reason the electrical impulse will propagate through the other ventricular muscle cells but at a slower rate resulting in a less synchronous contraction of the ventricular chambers and a less effective pumping action.

Disorders of the electrical functioning of the heart are important cause of morbidity and mortality. These disorders are generally termed arrhythmias. The proximate cause of approximately one-half of all cardiac deaths are due to arrhythmias. Arrhythmias can be thought as being caused by two general mechanisms.

One mechanism is disorders of impulse formation. One disorder of impulse formation involves abnormal automaticity of the heart's normal pacemaker. For example, failure of the sino-atrial node to form an impulse (sinus arrest), or forming impulses at too slow a rate (sinus bradycardia) or too fast a rate (sinus tachycardia). Abnormal automaticity also applies to the case when other sites in the heart (ectopic sites) begin to function as pacemakers initiating their own electrical impulses. For example, electrical activity may spread from an ectopic site in the atria to create premature atria depolarizations. If an ectopic site in the atria depolarizes repetitively at an accelerated rate an arrhythmia called atrial tachycardia may result. Similarly, an ectopic site in the ventricles may lead to the generation of premature ventricular depolarization or to the life-threatening arrhythmia called ventricular tachycardia.

A second mechanism is disorders of impulse conduction. One type of abnormal conduction is partial or complete block of the electrical impulse. For example, partial block affecting the atrio-ventricular node can abnormally slow impulses passing through the atrio-ventricular node or can result in some of the impulses not propagating through the node at all. Complete atrio-ventricular block is the condition that no impulses propagate through the node. Another type of abnormality of conduction is re-entry. Re-entry involves the circus movement of the electrical impulse through a region of the heart resulting in a self-sustaining pattern of electrical activity. Re-entry can occur in a regular fashion, for example, within a small site within the atria or ventricles. This type of micro-re-entry can be a cause of atrial tachycardia or ventricular tachycardia. Re-entry can also occur in a random disorderly pattern. Such random re-entry underlies atrial fibrillation and ventricular fibrillation.

There are various treatments for heart rhythm disturbances. Drugs can be used to alter the electrical conduction properties of the heart. Arrhythmias associated with too slow a heart rate (bradyarrhythmias) can often be treated by insertion of a pacemaker, but pacemakers are generally not effective in treating heart rhythm disturbances associated with too rapid heart rates (tachyarrhythmias).

Increasingly, a range of tachyarrhythmias are treated with radiofrequency (RF) ablation. In this technique, an electrode tipped catheter is applied to a specific location on the inner (endocardial) or outer (epicaridial) surface of the heart. Then radiofrequency energy is delivered through the electrode to heat the heart tissue near the electrode. The heating ablates the tissue so that it no longer can initiate or conduct electrical impulses. If the site is chosen properly the ablation can prevent the arrhythmia from recurring because the ablated site can either no longer initiate or no longer conduct the electrical impulse responsible for generating the arrhythmia.

While the use of RF ablation is rapidly increasing, there are many problems and limitations of the currently available methods and devices used for this procedure. These problems and limitations greatly limit the effectiveness and safety of RF ablation for the treatment of cardiac arrhythmias.

In order for RF ablation to be effective the site of ablation must be chosen precisely. Lengthy electrical mapping procedures using one or more catheters containing one or more electrical recording electrodes must be utilized in order to precisely locate the site to be ablated. These mapping procedures must be done in conjunction with the use of expensive imaging equipment. X-ray fluoroscopy was one of the first imaging modalities used for this purpose and is still widely used, but often now is used in conjunction with electroanatomic imaging systems (see for example, Emmanuel Koutalas, Sascha Rolf, Borislav Dinov, Sergio Richter, Arash Arya, Andreas Bollmann, Gerhard Hindricks and Philipp Sommer. Contemporary Mapping Techniques of Complex Cardiac Arrhythmias—Identifying and Modifying the Arrhythmogenic Substrate. Arrhythmia & Electrophysiology Review, 2015; 4(1):19-27 Access at: www.AERjournal.com).

Electroanatomic imaging involves using catheters that detect externally applied electrical or magnetic signals in order to define a three dimensional geometry of the heart chambers. Sometimes the electroanatomic images are merged with images obtained from magnetic resonance imaging (MRI) or from X-ray computerized tomography (CT).

Electroanatomic imaging modalities require purchase of very expensive equipment and long periods of time are required to create the images. Once the images are created then lengthy electrical mapping procedures are conducted to characterize the arrhythmia and to identify the site to be ablated.

Some electrical mapping methods involve the introduction of electrode arrays into the cardiac chamber to aid in the electrical mapping procedure. Generally, a different catheter is then used for ablating the target site. Often two or three catheters may be used in a single chamber during an ablation procedure. The multiple different types of specialized catheters employed further increase the complexity and cost of the procedure and its duration.

Often there is a specific localized site that is the source of an arrhythmia. As discussed above, this site may be an ectopic site that spontaneously depolarizes or a site of micro-reentry. Such sites may underlie, for example, atrial or ventricular premature depolarizations or atrial or ventricular tachycardia. In attempting to treat such arrhythmias by means of RF ablation, it may take many hours to create the images and conduct the electrical mapping to identify and accurately locate these sites.

The long duration of ablation procedures greatly increases the cost of performing these procedures. In addition, physicians and technicians involved in conducting these procedures must be very highly trained—this limits the availability of these procedures and also increases the cost. Furthermore, the long duration of the procedures is deleterious to patients, particularly patients who have some degree of heart failure that is quite common in patients with arrhythmias.

Failure to precisely locate the correct site to be ablated may result in failure to successfully block impulse formation, block impulse conduction or otherwise fail to prevent the arrhythmia from recurring or being re-induced while the patient is still lying on the catheterization laboratory. In addition, failure to precisely locate the correct site to be ablated may result in damage to cardiac tissue which should be preserved and may also lead to damage to adjacent structures.

Often even ablation procedures that appear to successfully abolish the arrhythmia while the patient is lying on the catheterization table, fail in that the arrhythmia recurs at a later time. For example, in a recent study (Packer D L et al, "Effect of Catheter Ablation vs Antiarrhythmic Drug Therapy on Mortality, Stroke, Bleeding, and Cardiac Arrest Among Patients With Atrial Fibrillation", Journal of the American Medical Society, doi:10.1001/jama.2019.0693 Published online Mar. 15, 2019) 17.1% of patients required a repeat ablation procedure during the first three months after the procedure. During the period starting 3 months after the initial ablation until three years later, 50% of patients had one or more episodes of atrial fibrillation or atrial flutter or atrial tachycardia. Recurrence rates of ventricular tachycardia after RF ablation treatment of ventricular tachycardia are similar (in the range of 30 to 70%) depending on the type of underlying heart disease (Liang J L, et al, "Long-term Outcomes of Ventricular Tachycardia Ablation in Different Types of Structural Heart Disease", Arrhythmia & Electrophysiology Review 2015; 4(3):177-83). Therefore, lack of long-term efficacy is a serious problem with current RF ablation procedures. These high recurrence rates may be due in part from a failure to identify the target site for ablation with sufficient precision.

A methodology currently being explored for ablation of cardiac tissue, but not yet in clinical practice, is irreversible electroporation (also known pulsed field ablation). In this methodology a short duration high voltage pulse, rather than RF energy, is applied to the cardiac tissue (see Fred H. M. Wittkampf, PhD; Vincent J. van Driel, MD; Harry van Wessel, BSc; Kars G. E. J. Neven, MD; Paul F. Grundeman, MD, PhD; Aryan Vink, MD, PhD; Peter Loh, MD, PhD; Pieter A. Doevendans, MD, PhD, Myocardial Lesion Depth With Circular Electroporation Ablation Circulation: Arrhythmia and Electrophysiology 2012; 5:581-586. Also see Reddy V Y, Neuzil P, Koruth J S, Petru J, Funosako M, Cochet H, Sediva L, Chovanec M, Dukkipati S R, Jais P, Pulsed Field Ablation for Pulmonary Vein Isolation in Atrial Fibrillation, Journal of the American College of Cardiology (2019), doi: https://doi.org/10.1016/j.jacc.2019.04.021).

In the method of ablating cardiac tissue by means of irreversible electroporation, the short duration (for example the majority of the energy in the pulse is contained in a window of less than 20 milliseconds duration), high voltage (for example between 250 and 2,500 volts peak amplitude) pulse is administered to the cardiac tissue through an electrode mounted on a catheter. The pulse may be monophasic, biphasic pulse or polyphasic. It is thought that the pulse creates pores in the cell membranes of the cardiac tissue that results in the cells dying via an apoptosis mechanism.

Another method of ablating cardiac tissue is cryoablation in which the tissue is cooled sufficiently to irreversibly eliminate electrical conduction or impulse formation.

Thus, provided herein is a low cost, rapid means of accurately locating and ablating sites to treat cardiac arrhythmias. Additionally, methods and apparatuses are provided that can utilize a single catheter both for the electrical mapping and ablation procedures.

In one embodiment of a method to locate and ablate the source of an arrhythmia (see FIG. 1), a catheter containing an array of electrodes is introduced into the body. At least one of the electrodes must be capable of delivering ablative energy to biological tissue. In one embodiment, the catheter is introduced into the cardiovascular system through an artery or a vein and is placed inside one of the cardiac chambers to access the inner (endocardial) surface of the heart. In another embodiment, the catheter may be introduced through the chest wall to access the outer (epicardial) surface of the heart.

The catheter is then positioned so that some or all of the electrodes are in contact with cardiovascular tissue and then an X-ray image is taken.

The locations of the electrodes as seen on the X-ray image are then measured. This measurement may either be accomplished manually or by means of computer analysis using software adapted to this purpose. To aid in this process, the catheter may contain radio-dense markings visible on X-ray to assist in identifying which electrode is which (see FIG. 8).

If the arrhythmia does not occur spontaneously, then an operator may need to induce the arrhythmia by electrically stimulating the heart.

Then the activity signal sensed by the electrodes are recorded. Once enough signal data has been recorded, the operator may need to terminate the arrhythmia by electrically stimulating the heart.

The recorded signals are then processed to determine the times of arrival at each of the electrodes of an electrical impulse emanating from the arrhythmia source. This may be accomplished by computer analysis using software adapted to this purpose and/or by manual measurement.

The Arrhythmia Source Localization Procedure (see FIG. 2) is then employed. This procedure inputs the locations of the electrodes on the X-ray image and the arrival times. This procedure then computes the location of the arrhythmia source on the X-ray image, the conduction velocity, and the distance of the ablation electrode to the arrhythmia source. The procedure then outputs these.

Then the location of the arrhythmia source on the X-ray image outputted from the Arrhythmia Source Localization Procedure is displayed on the X-ray image.

If the computed distance of the ablation electrode to the arrhythmia source is less than or equal to a threshold value (for example, 2 millimeters) then the ablation electrode is used to deliver ablation energy to the arrhythmia source.

If the computed distance of the ablation electrode to the arrhythmia source is greater than the threshold value, then under X-ray guidance the catheter is moved so that the electrodes are in contact with tissue and in particular the ablation electrode is in close proximity to the arrhythmia source on the X-ray image. Serial X-ray images may be displayed to help guide the operator in moving the catheter. The location of the arrhythmia source is displayed on each X-ray image which will also display the location of the ablation electrode so the operator can track his/her progress in moving the ablation electrode towards the arrhythmia source.

Then one goes back to the step of measuring the new electrode locations on the X-ray image. This process continues until in the paragraph above the computed distance of the ablation electrode to the arrhythmia source is less than or equal to a threshold value at which point the ablation electrode is activated to ablate the arrhythmia source. Activation of the ablation electrode involves delivering ablative energy to the electrode. The ablative energy may be, for example, radiofrequency electrical energy or electrical energy configured to irreversibly electroporate the tissue.

FIG. 2 shows the Arrhythmia Source Localization Procedure. This procedure is a computational procedure, which may be implemented in computer software, is described below.

This procedure inputs the measured coordinates of the locations of the electrodes on the 2-dimensional X-ray image and the times of arrival at each of the electrodes of an electrical impulse emanating from the arrhythmia source.

Using numerical methods well known in the art, the procedure positions in space, and determines the angular orientation of, a simulated model of the electrode array so that a scaled projection of the locations of the model's electrodes onto the plane of the X-ray image ("X-ray plane") is consistent with the measured locations of the electrodes on the X-ray plane.

The simulated model of the electrode array is based on the known geometry and dimensions of the array.

A scale factor is introduced in the above computation when computing the projection of the simulated model electrode array onto the X-ray plane. The scale factor is one of the unknowns whose value is computed in the above process. Introduction of the unknown scale factor is necessary since in general distances in the X-ray plane are measured in arbitrary uncalibrated units and also the magnification factor of the X-ray image is in general unknown.

In general, in terms of the aspect of the computation relating to the positioning in space of the simulated model of the electrode array, it is sufficient to position one point on the array (for example, the location of a central electrode or of an ablation electrode) in 2-dimensions on a plane parallel to the X-ray plane so that the position coincides with the 2-dimensional projected location of the point on the X-ray plane. The value of the third coordinate of the point, perpendicular distance to the X-ray plane, in general need not be determined and may not be calculable. The angular orientation of the simulated model array can be computed relative to the above selected point on the array.

Once the angular orientation of the electrode array is determined in the above computation, the orientation of the tissue plane on which the electrode array lies is known as well. The tissue plane is the same as the plane of the electrode array itself. Once the position and angular orientation of the electrode array is computed, the locations of the electrodes on the tissue plane can be directly computed from the known geometry and dimensions of the array. Without loss of generality, the origin of the tissue plane may be defined as the location of the point on the simulated array used in the positioning step above.

A numerical search over the tissue plane is performed to determine the location of the arrhythmia source on the tissue plane which is consistent with the locations of the electrodes on the tissue plane and the inputted arrival times assuming a constant velocity of the impulse along the surface of the plane. This procedure yields the location of the arrhythmia source on the tissue plane as well as the value of the conduction velocity. Since the actual dimensions of the electrode array are known, it is possible to compute the location of the arrhythmia source on the tissue plane as measured in absolute distance units relative to the location of the array and also measure the conduction velocity in absolute units of distance divided by time. In particular, the distance of the arrhythmia source from an ablation electrode on the array may be determined. From the location of the arrhythmia source on the tissue plane and the previously determined position and angular orientation of the tissue plane and the scale factor, the procedure computes the location of the arrhythmia source as projected on the X-ray image. Then the computed location of the arrhythmia source on the X-ray image, the computed conduction velocity, and the computed distance of the ablation electrode to the arrhythmia source may be outputted and the procedure terminated.

The apparatus used to implement the methods discussed herein is shown in FIG. 3. The apparatus includes a computer to perform the processing. The computer is connected to a display. In addition, an imaging system is used to image the catheter and electrodes inside the chest. The imaging system may be an X-ray fluoroscopic system. In some embodiments the imaging system maybe an electroanatomic imaging system.

The apparatus includes a catheter containing an array of electrodes. In one embodiment (see FIGS. 4 through 7) on the distal end of the catheter there is a central electrode which may be used for both recording and ablation. In addition, in this embodiment on the distal end of the catheter there is mounted a set of deployable wings each of which contains one or more electrodes. In the longitudinally expanded mode the deployable wings are collapsed along the shaft of the catheter and in the longitudinally compressed mode the deployable wings are expanded transversely to the shaft of the catheter and surround the central electrode. The catheter will contain means of longitudinally expanding and compressing the deployable wings. In addition, the catheter will contain means of irrigating one or more ablation electrodes and will contain means of measuring the temperature of the ablation electrode.

Figure 4:
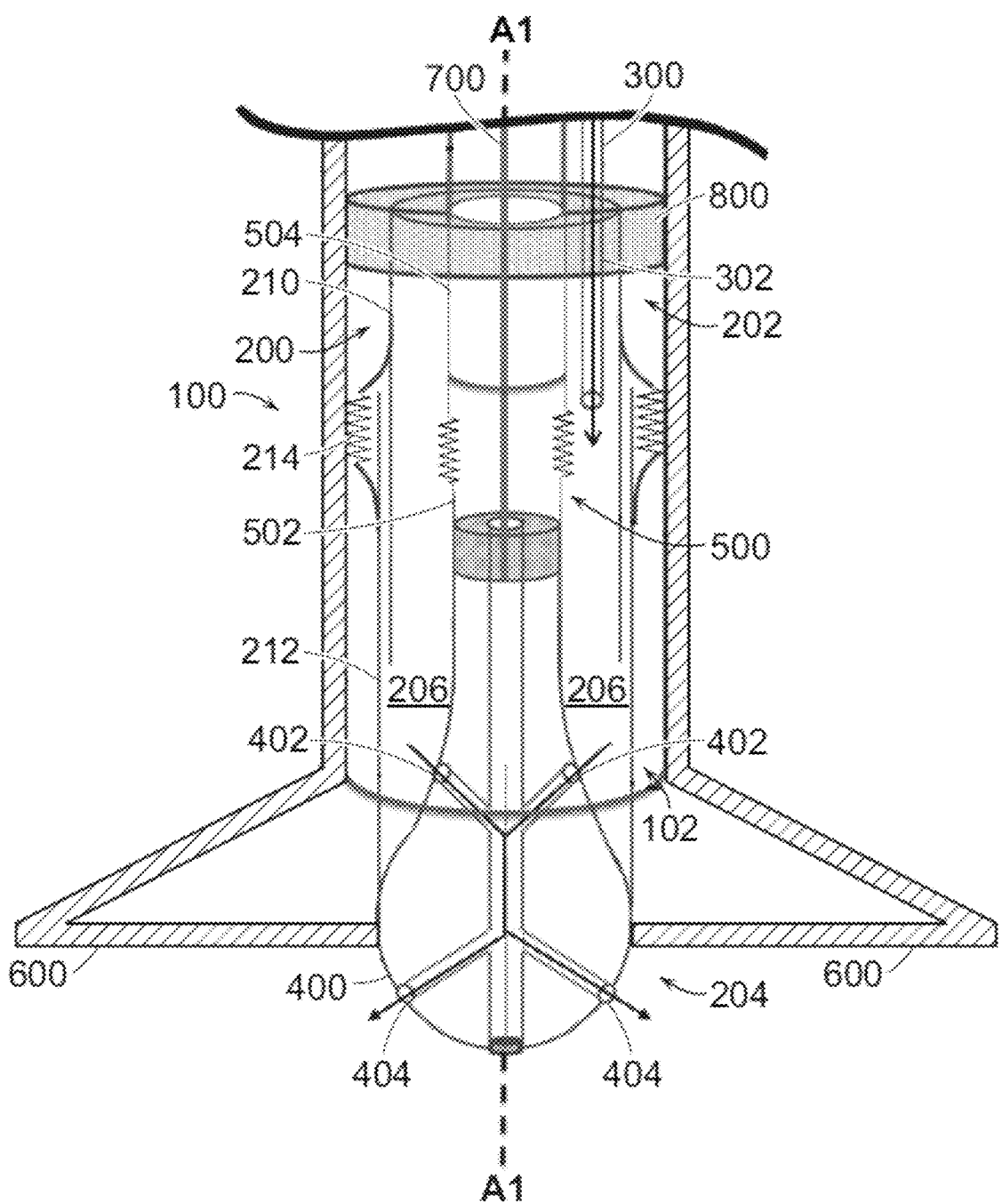
FIG. 4 is a cross-sectional, partially-perspective side view of one embodiment of a distal end of a catheter with deployable wings compressed longitudinally and expanded transversely to the catheter shaft.
Figure 5:
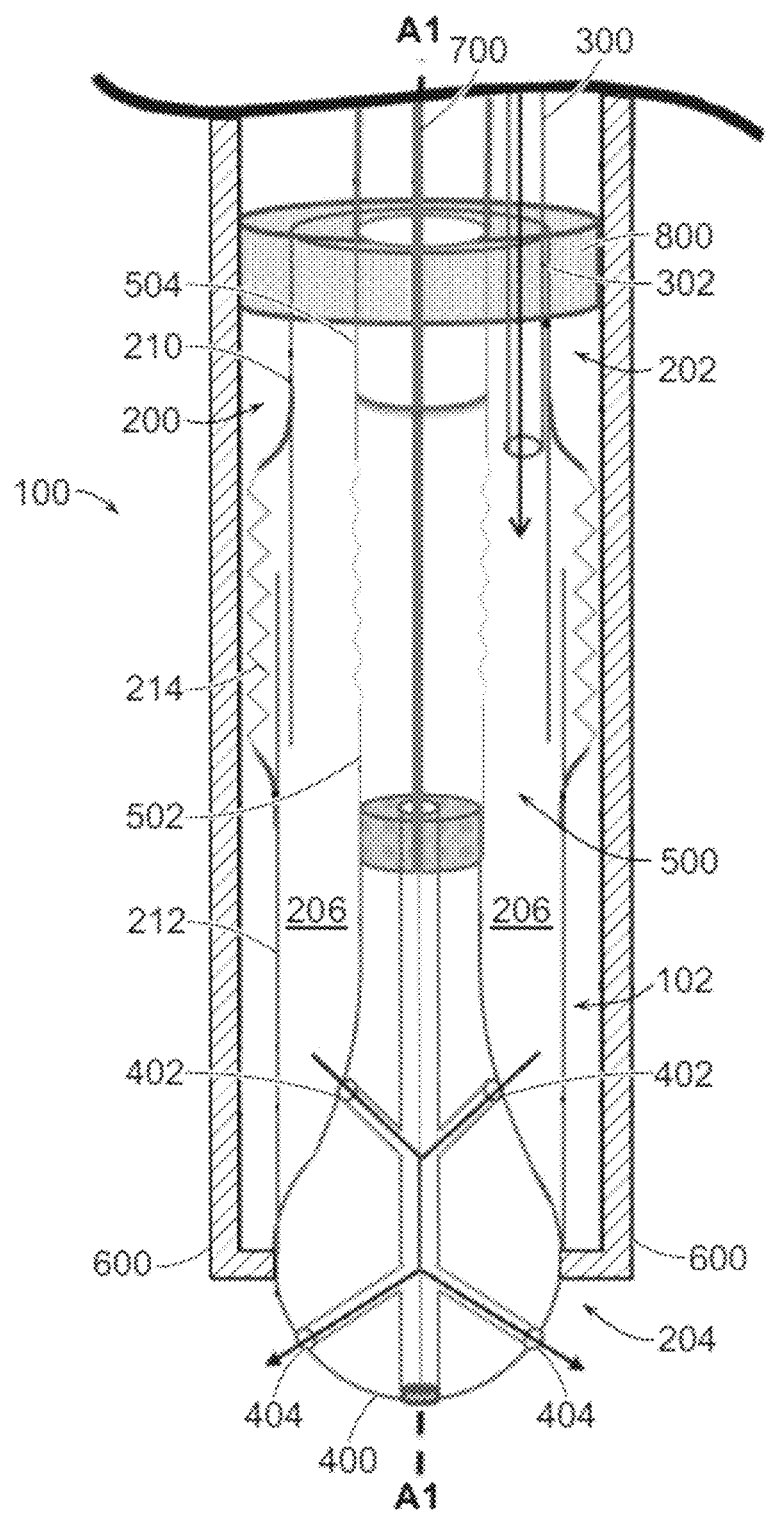
FIG. 5 is a cross-sectional side view of the distal end of the catheter of FIG. 4 in a longitudinally expanded state with deployable wings collapsed onto the catheter shaft.

For example, FIGS. 4-7 illustrate one embodiment of a distal end of a catheter with an elongate body 100. The elongate body 100 can be flexible and can have a proximal end, a distal end, and a lumen extending at least partially therethrough. An end effector 102 is disposed at least partially within the distal end of the elongate body 100. The end effector 102 can include an expandable and contractible housing 200 having a fluid inlet 302 at a proximal end and an electrode 400 at a distal end thereof and defining a fluid outlet in the form of at least one pathway formed therethrough. A fluid delivery tube 300 can extend through the elongate body 100 for delivering fluid to the housing 200. The catheter can also include at least one expandable member or wing 600 extending between the distal end of the elongate body 100 and the electrode 400, and an actuator 700 coupled to the electrode for actuating the end effector 102. In this embodiment, proximal movement of the actuator 700 can cause the electrode 400 to retract proximally, thereby causing the expandable member or wing(s) 600 to expand, as shown in FIG. 4, and distal movement of the actuator can cause distal advancement of the electrode body 100, which can cause the expandable member or wing(s) 600 to collapse or compress into a linear configuration, as shown in FIG. 5. For example, the catheter with the elongate body 100 can be maneuvered to a surgical site in the collapsed, linear configuration. When at a treatment site, the catheter can either treat tissue in the linear configuration or it can be deployed into the expanded configuration.

The end effector can have a variety of configurations, but as indicated above the end effector can be configured to allow advancement and retraction of the electrode using the actuator, while also allowing fluid to be delivered to the electrode. In the illustrated embodiment, the expandable and contractible housing 200 forms a proximal portion of the end effector with the electrode positioned at the distal end thereof. The expandable and contractible housing 200 can have a variety of configurations, but in an exemplary embodiment it is at least partially disposed in the elongate body 100 and at least a portion of it can be configured to move relative to and extend from the distal end of the elongate body 100. The housing 200 can be positioned co-axially with the elongate body 100 such that a longitudinal axis of the housing 200 corresponds to a longitudinal axis A1 of the elongate body 100. In order to define a fluid sealed lumen 206 extending therethrough, a distal end 204 of the housing 200 can be fixed to the electrode 400, and a proximal end 202 of the housing 200 can be sealed by and fixed within the elongate body 100. For example, a heat treatment can be applied to the elongate body to form a substantial end cap 800 on the housing 200, as will be discussed in more detail below. As indicated above, the housing 200 can be configured to expand and contract as the electrode 400 is pulled proximally and pushed distally during use. As illustrated in FIG. 4, the housing 200 can include an upper shaft or tube 210, a lower shaft or tube 212, and an expansion member 214. A proximal end of the expansion member 214 can be attached to the upper shaft 210, and a distal end of the expansion member 214 can be attached to the lower shaft 212. The upper shaft 210 can be fixed at its proximal end to the elongate body 100 and the lower shaft 212 can be fixed to the electrode 400, and one of the upper and lower shafts 210, 212 can be slidably disposed within the other one of the upper and lower shafts 210, 212. As a result, the lower shaft 212 can be configured to slidably move towards and away from the upper shaft 210 in coordination with to movement of the electrode 400. Such a configuration allows the housing 200 to expand and contract. As shown in FIG. 4, a distal end of the upper shaft 210 and a proximal end of the lower shaft 212 overlap one another when the housing 200 is in a deployed state. As shown in FIG. 5, the upper shaft 210 and the lower shaft 212 are moved away from each other in a linear state.

While the upper and lower shafts 210, 212 can be configured to sealing engage one another to prevent fluid leakage from the housing 200, in an exemplary embodiment the expansion member 214 forms a seal around the engagement portion between the two shafts 210, 212. The expansion member 214 can be configured to expand between the two shafts 210, 212 as the shafts 210, 212 slidably move away from each other, and to compress as the shafts 210, 212 move toward one another. The expansion member 214 will thus allow movement of the shafts 210, 212 while maintaining a seal in the fluid sealed lumen 206 within the housing 200 when the housing is in the expanded state or the contracted state. In certain aspects, a length of each of the shafts 210, 212 can be minimized because the expansion member 214 can prevent disengagement between the shafts 210, 212 in the expanded state while still providing a fluid sealed lumen 206 in the housing 200. Because lengths of the shafts 210, 212 can be minimized, an overall length of the housing 200 can be minimized, which allows for a smaller overall end effector length and thus more flexibility of the catheter.

The shafts 210, 212 can be made of stiffer materials relative to the expansion member 214, such as plastics, elastomers, metals, etc., and the expansion member 214 can be made of stretchable and compressible material, such as balloon-like materials, elastomers, plastics, etc. The expansion member 214 can have a variety of forms. For example, the expansion member 214 can be a stretchable, elastic tube. In some situations, a volume of an elastic tube can change when it is stretched, which can result in blood being sucked into the catheter when the catheter configuration is moved between a deployed state and a linear state. This can result in the formation of clots in the fluid compartment. Such clots might subsequently be expelled into the blood stream. Thus it can be helpful to provide support to the elastic tube by providing a support structure, using a more rigid material, etc. The expansion member 214 can be made of a more rigid material that can be folded accordion style. The internal volume of such a tube can experience less change when its length is altered compared to an elastic tube. However, when its length is shortened, the expansion member 214 can potentially fold over on itself, thus impeding fluid flow through the catheter. The expansion member 214 can thus have a central longitudinal support element therein to provide support and prevent incorrect folding and/or collapse. For example, one or both of the shafts 210, 212 can also serve as supports to the expansion member 214 when the housing 200 moves to the contracted state, allowing the expansion member 214 to fold in an orderly controlled manner, similar to an accordion, rather than collapsing in on itself and potentially blocking the fluid sealed lumen 206 of the housing 200. However, the central longitudinal support element is not limited to one or both of the shafts 210, 212. For example, the central longitudinal support element can include one or more other catheter elements, such as the actuator 700, a wire connected to a temperature sensor (such as a thermocouple) located in a tip of the catheter, a tube containing the actuator and/or thermocouple wire, etc. Because the stretchable tube is prevented from folding over on itself, fluid flow through the catheter in general and the expansion member 214 in particular is not impeded by such folding. In addition, in embodiments where the central longitudinal support element is a tube containing other catheter elements, such as the actuator wire or the wire connected to a thermocouple, these other elements can be isolated from the irrigation fluid and thus any adverse effects on the function of these elements that would result from contact with the irrigation fluid can be minimized. In some embodiments, a portion of the central longitudinal support element itself can include a stretchable element that can serve to reduce or prevent leaks around the actuator wire and/or thermocouple wire. A variety of other supports can be used with the expansion member 214, such as tubes, braces, stiffer materials, pre-formed or folded material that will maintain a more rigid accordion fold when contracted, etc. The fluid sealed lumen 206 can be configured to allow delivery of fluid to the electrode 400 with more consistent flow rates and more ideal fluid pressures, thus helping to provide a smoother function of the device and better irrigation and ablation of tissue.

As indicated above, the proximal end 202 of the housing 200 can be coupled to the elongate body 100, and can be fluidly sealed to prevent any fluid from moving proximally from the fluid sealed lumen 206 of the housing into other proximal parts of the catheter. The proximal end 202 of the housing 200 can be coupled to the elongate body 100 through a variety of means. For example, the elongate body 100 can be heat treated, causing the elongate body 100 to melt around and across an open proximal end of the housing 200, as well as around other components extending therethrough, such as the fluid delivery tube 300 and a sealing shaft 500 that receives the actuator. The process of heating can seal the proximal end 202 of the housing 200, forming a cap 800 of melted material and achieving fixation and a fluid seal through one process. A variety of other means for both fixation and sealing can be used, however. For example, the proximal end 202 of the housing 200 can be sealed using a cover, a separate and distinct cap, seal, etc., placed across the opening of the proximal end 202 of the housing 200. An end cap or cover can also be formed as part of the upper tube.

As indicated above, the housing 200 is configured to receive fluid therein and to direct fluid to the electrode. Fluid can be introduced to the housing 200 through a variety of means, such as via a fluid delivery tube 300 extending through an inlet formed in the sealed proximal end of the housing 200. The fluid delivery tube 300 can be configured to deliver fluid through the catheter and into the fluid sealed lumen 206 of the housing 200. The fluid delivery tube 300 can at least partially extend through the catheter and the elongate body 100, for example extending from a proximal end of the catheter and terminating in the fluid sealed lumen 206 of the housing 200. The cap 800 can be formed after the fluid delivery tube 300 is in place, thus sealing the proximal end 202 of the housing 200 and securing the fluid delivery tube 300 in place. However, the fluid delivery tube 300 can be configured to pass through a variety of covers over the proximal end 202 of the housing 200 and can be secured in place through a variety of means, such as by use of adhesive or pins. The fluid delivery tube 300 can be configured to deliver a consistent flow of fluid into the fluid sealed lumen 206.

The electrode 400 can be positioned at a distal end of the elongate body 100, and it can be configured to move between a proximally deployed or vector position to an advanced or linear position. In the retracted position, the electrode 400 can be at least partially retracted into the elongate body 100, and in the expanded position, the electrode 400 can extend distally away from the distal-most end of the elongate body 100. A proximal end of the electrode 400 can be at least partially disposed in the distal end 204 of the expandable and contractible housing 200, expandable along its longitudinal dimension such that it is stretchable. For example, the lower shaft 212 of the housing 200 can attach to the electrode 400 such that a fluid seal can be formed along the engagement of the electrode 400 and the lower shaft 212. This engagement can seal the distal end of the fluid sealed lumen 206 of the housing 200. The electrode 400 can be configured to be moved distally and proximally, which can cause the housing 200 to expand and contract as the lower shaft 212 moves distally and proximally with the electrode 400. The electrode 400 can have one or more fluid paths therethrough configured to allow fluid flow from the fluid sealing lumen 206 to a position distally external from the entire catheter to reach tissue to be irrigated and/or ablated. For example, the electrode 400 can have one or more inlet ports 402 on a proximal half thereof that open inside of the fluid sealed lumen 206 of the housing 200 and connect via one or more fluid channels within the electrode 400 to outlet ports 404 on a distal half thereof that open outside of the catheter entirely. The electrode 400 can thus be configured to receive fluid through the inlet ports 402 from the fluid sealed lumen 206 of the housing 200 and can be configured to expel the fluid from the outlet ports 404 to tissue that is distally positioned in front of the electrode 400. Because the electrode 400 can be sealed to the housing 200 at the distal end of the fluid sealed lumen 206 and because the housing 200 can expand and contract with the electrode 400, irrigation can be performed when the electrode 400 is retracted or advanced (e.g. in either of the deployed or linear states shown in FIGS. 4 and 5).

In order to move the electrode, the end effector 102 can be actuated through a variety of means, such as by use of the actuator 700. The actuator 700 can have a variety of forms, such as one or more wires and/or cables. The actuator 700 can extend through the elongate body 100 between a proximal end of the catheter and the end effector 102. The actuator 700 can extend through the lumen 206 of the housing 200 and can be fixed to a proximal end of the electrode 400. The actuator 700 can be slidable relative to the elongate body 100 such that the actuator 700 can slide distally and proximally while the elongate body 200 remains unmoved relative to the actuator 700. The actuator 700 can be in the form of a wire that is rigid enough to push the electrode 400 distally into the extended state, and strong enough to pull the electrode 400 proximally into the retracted state, while still being flexible enough to extend through bending and angled sections of the catheter. The actuator 700 can include an electrically-conductive wire that can deliver energy to the electrode 400 during tissue ablation. The actuator 700 can also have one or more coatings thereon to protect surrounding components from the electrical energy deliverable through the actuator 700 and to protect the actuator 700 from its surrounding environments.

In order to allow the actuator to couple to the electrode, the actuator 700 can be co-axial with the housing 200. The actuator 700 can be configured to extend through the proximal end 202 of the housing 200 and through the fluid sealed lumen 206 to engage with the proximal end of the electrode 400 such that the actuator 700 is slidable relative to the proximal end 202 of the housing 200 while the fluid seal of the fluid sealed lumen 206 is maintained. The fluid seal of the fluid sealed lumen 206 can be maintained even with the slidable actuator 700 disposed therein through a variety of means. For example, a sealing shaft 500 can extend around at least a portion of the actuator 700 and can be configured to create a fluid barrier between the actuator 700 and fluid in the end effector 102, such as the fluid sealed lumen 206. The sealing shaft 500 can extend at least partially through the end effector 102, for example extending from the electrode 400, through the fluid sealed lumen 206 of the housing 200, to the proximal end 202 of the housing 200, and optionally into the proximal part of the catheter. The actuator 700 can extend through a lumen within the sealing shaft 500, and the sealing shaft 500 can thus prevent the fluid in the fluid sealed lumen 206 of the housing 200 from contacting the actuator 700. For example, a distal end of the sealing shaft 700 can be sealably fixed to the proximal end of the electrode 400, and a proximal end of the sealing shaft 500 can extend into and optionally through the proximal end 202 of the housing. The sealing shaft 500 can be fixed in place relative to the proximal end 202 of the housing 200. For example, when the cap 800 is formed, the sealing shaft 500 can be positioned before formation and fixed in place relative to the proximal end 202 of the housing during cap formation. However, the sealing shaft 500 can also be fixed in place through a variety of other means, such as adhesives, pins, engagement with other seals, caps, or covers added to the proximal end 202 of the housing 200, etc.

The sealing shaft 500 can be configured to expand and contract with the housing 200 as the electrode 400 is moved distally and proximally. Because the sealing shaft 500 is able to expand and contract with movement of the electrode 400, the sealing shaft 500 can be configured to provide a sealed passage for the actuator 700 through the fluid sealed lumen 206 of the housing 200, which can protect the actuator 700 and can allow the lumen 206 in the housing 200 to remain fluid sealed even as the actuator 700 is moved back and forth through the proximal end 202 of the housing 200. Without the sealing shaft 500, pressure from the fluid flowing into the housing 200 could cause fluid to flow through the opening in the proximal end 202 of the housing 200 around the actuator 700, and into the rest of the catheter. The required movement of the actuator 700 through the proximal end 202 of the housing 200 makes fluidly sealing the proximal end 202 through other means, such as by use of O-rings, difficult to achieve and consistently maintain. In particular, O-rings or other seals will create friction, thereby preventing movement of the actuator. Accordingly, the sealing shaft 500 allows for free movement of the actuator 700, while fluidly separating the actuator 700 from the fluid sealed lumen 206 of the housing 200, thus allowing fluid to be delivered directly to the electrode.

The sealing shaft 500 can include a flexible sealing portion that is configured to expand and contract with movement of the actuator 700 and the electrode 400. In the illustrated embodiment, a sealing member 502 forms a distal portion of the sealing shaft 500 and is sealed on its distal end to the proximal end of the electrode 400. The proximal end of the sealing member 502 can be sealed to a rigid portion 504 of the sealing shaft 500 that can extend through the proximal end 202 of the housing 200. However, the sealing member 502 can also be sealed directly to the proximal end 202 of the housing 200 and/or a cap, cover, seal, etc. that is used to close the proximal end 202. Alternatively, the sealing member 502 can be integral and unitary with the sealing shaft 500.

When the actuator 700 is moved proximally and distally to move the electrode 400 between the contracted and the expanded states, the sealing member 502 is configured to stretch and contract with movement of the actuator 700 so that the electrode 400 can be moved without breaking the fluid barrier between the fluid sealed lumen 206 of the housing 200, the proximal end 202 of the housing 200, and the actuator 700. The sealing member 502 can be made from any material that can expand and contract, such as various elastomers, plastics, elastics, balloon-like materials, etc. The sealing shaft 500 can also have a rigid portion 504 that extends through the proximal end 202 of the housing 200 and that is configured to be secured in place by the cap 800. The rigid portion 504 can be made of a variety of materials that are configured to withstand the heat treatment applied to the elongate body, such as various plastics or metals.

As indicated above, the catheter also includes at least one expandable member extending between the electrode and the distal end of the elongate body. In an exemplary embodiment, the catheter can include four expandable members positioned equidistant there around. As the electrode 400 advances and retracts, the expandable members 600 that extends between the distal end of the elongate body 100 and the electrode 400 moves between an initial linear configuration for advancement through a body lumen, to flared or expanded configuration. In the deployed configuration, the expandable members can bend around a midpoint there along to extend substantially perpendicular relative to the elongate body 100, forming a flower pedal shape or propeller blade shape around the electrode 400. The one or more expandable members 600 can be configured to extend longitudinally relative to the elongate body 100 when the electrode 400 is extended distally away from the elongate body 100. As the electrode 400 and the distal end 204 of the housing 200 extend distally, the expandable members 600 can be configured to flatten against an exterior surface of the housing 200 as the distal end of the catheter takes on a linear shape. The distal ends of the one or more expandable members 600 can couple to the electrode 400 at a point between the proximal and distal end of the electrode 400, such as at a point corresponding to the engagement between the distal end 204 of the housing 200 and the electrode 400.

The expandable members 600 can each have one or more electrodes disposed thereon, such as for recording electrical signals, and positioned on a distal portion of the expandable member 600 such that each electrode is configured to be approximately perpendicular to the elongate body 100 when the electrode 400 is retracted in the contracted state and each expandable member 600 is in a flared or winged state. The one or more electrodes on the expandable members 600 can be configured to operate in coordination with electrode 400 to provide ablation to a larger surface area of tissue than just the electrode 400 alone. Additional details concerning the catheter generally and the interaction between the expandable member(s) and a central electrode are discussed in detail in U.S. Pat. No. 8,882,761, filed Jul. 15, 2008, U.S. Pat. No. 9,717,558, filed Nov. 7, 2014, and patent application Ser. No. 15/661,606, filed Jul. 27, 2017, all of which are hereby incorporated by reference herein in their entireties. The electrode(s) on the one or more expandable members 600 can be coupled to and receive energy from the actuator 700.

Figure 6A:
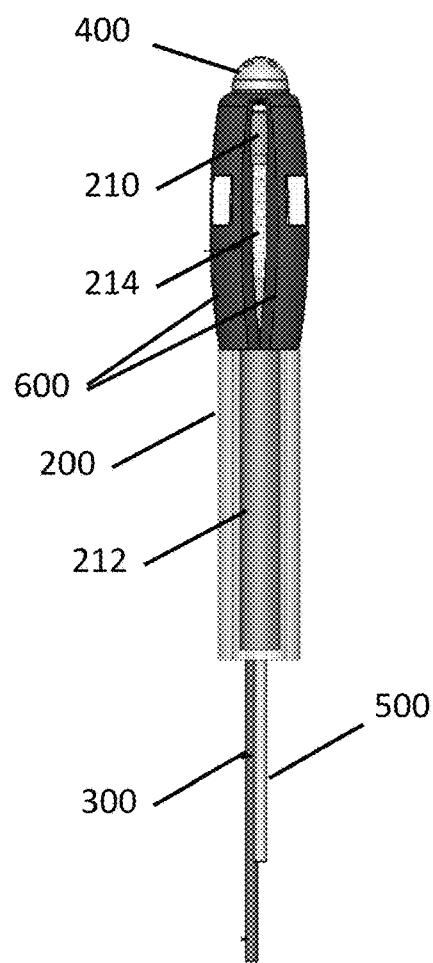
FIG. 6A is a partially transparent and partially cutaway side illustration of the catheter shown in FIG. 4 and FIG. 5.
Figure 6B:
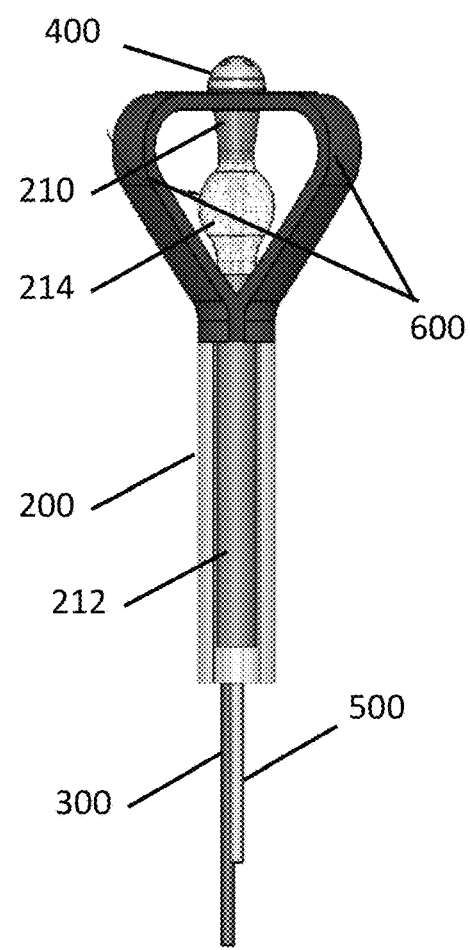
FIG. 6B is another partially transparent and partially cutaway side illustration of the catheter shown in FIG. 4 and FIG. 5.
Figure 6C:
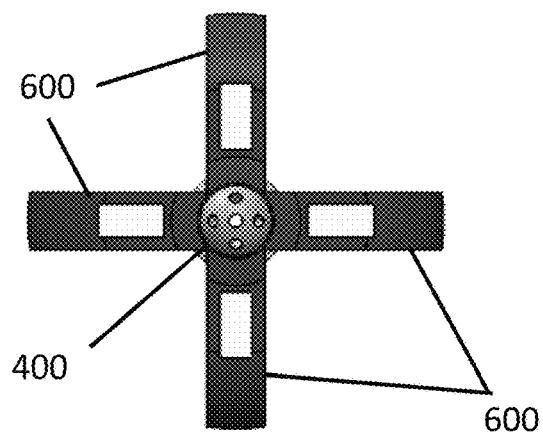
FIG. 6C is a front view of the catheter shown in FIG. 4 and FIG. 5.
Figure 7:
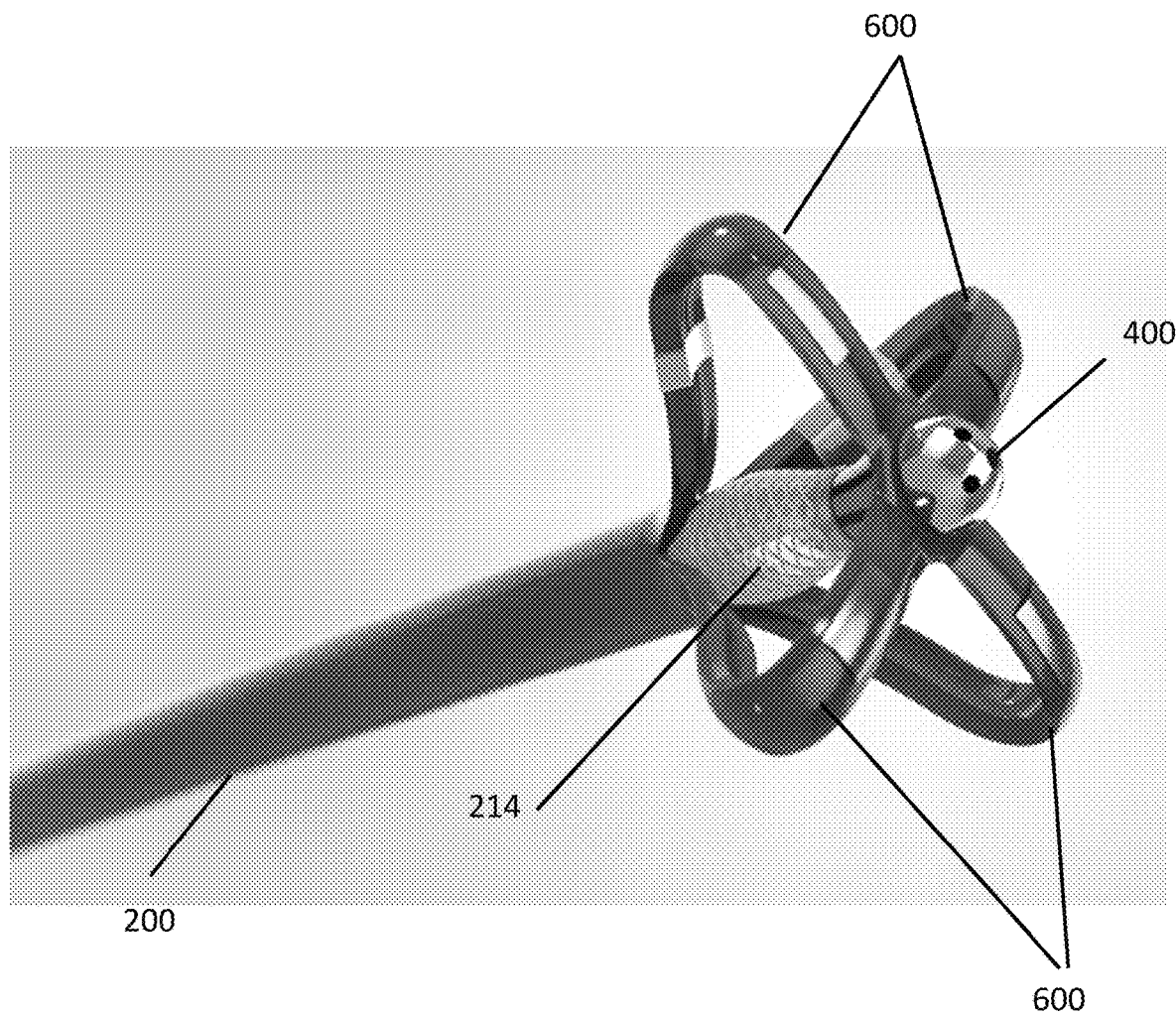
FIG. 7 illustrates the catheter shown in FIGS. 6A-6C in a longitudinally compressed mode.
Figure 8:
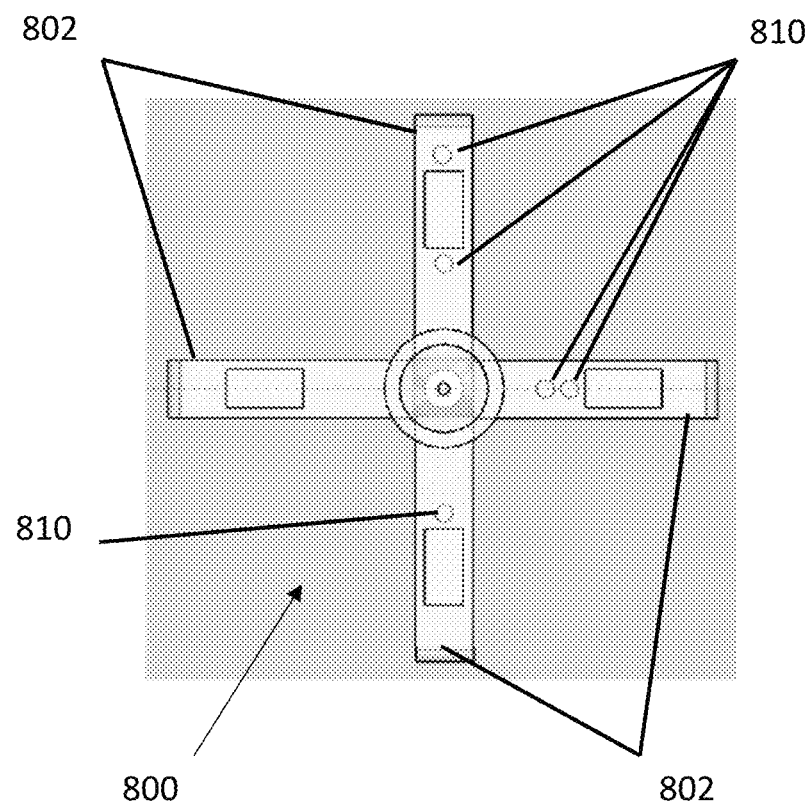
FIG. 8 shows the presence of radio-dense markers embedded in the deployable wings of the type of catheter shown in FIGS. 4 through 7 in the form of small circular disks.

Thus FIGS. 6A-6C illustrate an irrigated ablation catheter that may be used in a method provided herein. It can have a shaft containing an irrigation tube to deliver irrigation fluid to a central ablation electrode located on the tip of the shaft. There are four deployable wings on the catheter each containing a recording electrode. The deployable wings may deployed in a longitudinally expanded mode or a longitudinally compressed mode. In the longitudinally expanded mode the deployable wings are collapsed along the shaft of the catheter and in the longitudinally compressed mode the deployable wings are expanded transversely to the catheter shaft and surround the central ablation electrode. An actuator cable which passes through the center tube is used to move the catheter between longitudinally expanded and longitudinally compressed modes. The irrigation fluid passes from the irrigation tube through an expandable sheath to enable irrigation of the central electrode in either the longitudinally expanded or compressed modes. Wires passed through the central tube connect to the central ablation electrode and each of the recording wing electrodes. Also, a wire pair is connected to a thermocouple located in the central ablation electrode. FIG. 8 shows the presence of radio-dense markers embedded in the deployable wings of the type of catheter shown in FIGS. 4 through 7. Here the markers are illustrated as small circular disks. The number and location of the markers enable an operator to determine which electrode is which when seen on an X-ray image.

In use, the end effector 102 can be arranged in the linear state as shown in FIG. 5 and the catheter can be advanced through a body lumen of a patient to position the end effector 102 at a surgical site with tissue to be treated, such as tissue requiring ablation and/or irrigation. The actuator 700 can be proximally retracted to proximally retract the electrode 400, causing the end effector 102 to move to the deployed state, as illustrated in FIG. 4, with the expandable members in the expanded configuration. As the electrode 400 is retracted, the housing 200 compresses and reduces in length as the shafts 210, 212 move towards each other and overlap with one another and the expansion member 214 contracts before folding over one or both of the shafts 210, 212 as it compresses entirely. The sealing member 502 of the sealing shaft 500 can also begin compressing and folding together as the actuator 700 retracts the electrode. The catheter can be manipulated to position the electrode 400 and one or more of the expandable members 600 in contact with tissue to be treated. The catheter can be actuated to deliver energy to the electrode 400 and any electrodes arranged on the expandable members 600 and/or to deliver fluid through at least one fluid pathway in the electrode 400. The fluid can flow through the fluid sealed lumen 206 and through the ports 402, 404 in the electrode. When ablation and/or irrigation is finished, the actuator 700 can be pushed distally to cause the end effector 102 to return to the linear state. The housing 200 can expand in length as the shafts 210, 212 move away from each other and the expansion member 214 expands to keep the shafts 210, 212 engaged with each other while allowing the shafts 210, 212 to move away. The sealing member 502 of the sealing shaft 500 also can unfold and expand as the electrode 400 moves distally. The catheter can be maneuvered to another site or removed from the patient. Because of the expandable and contractible fluid channel in the end effector 102, fluid can be successfully delivered to tissue with the end effector 102 in the expanded state, allowing ablation with fluid and/or irrigation to be performed successfully in the expanded state. The catheter(s) disclosed herein can be steered through a variety of means, which are well-known in the art.

While an exemplary catheter is provided above, the ablation procedure provided herein can be implemented using a variety of catheters, such as those described in US Patent Application Publication No. 2019/0090942 entitled "Catheter and Method for Improved Irrigation" and filed on Sep. 24, 2018; U.S. Pat. No. 8,882,761 entitled "Catheter and method for improved ablation" and filed on Jul. 15, 2008; U.S. Pat. No. 9,717,558 entitled "Catheter and method for improved ablation" and filed on Nov. 7, 2014; and US Patent Published Application No. 2017/0319274 entitled "Catheter and Method for Improved Ablation" and filed on Jul. 27, 2017, all of which are hereby incorporated by reference.

In one embodiment, deployable wings 802 of a catheter 800 similar to catheter 100 contain radio-dense markers 810 (see FIG. 8). These markers may be seen on an X-ray and enable an operator to determine which electrode is which. This is important when measuring the locations of the electrodes on the X-ray image so that the operator knows which electrode location corresponds to which electrode.

The apparatus also includes an element to amplify and filter the electrical signals recorded from the catheter's electrodes and an element to convert the resulting analog signals to digital signals that may be imported into the computer.

In addition, the apparatus includes an energy source for ablating biological tissue. This energy source is connected to the catheter and through one or more wires in the catheters to one or more ablation electrodes. In one embodiment, the ablation energy source may generate radiofrequency electrical energy. In another embodiment, the ablation energy source may generate electrical energy configured to irreversibly electroporate biological tissue. The energy source in addition to delivering ablative energy to one or more ablation electrodes through the catheter, may also receive signals from the catheter that are in turn used to control the delivery of ablative energy back to the catheter. Such signals may include the temperature of one or more ablation electrodes and the electrical impedance of one or more electrodes.

The various elements of the apparatus will be connected to each other through appropriate interfaces indicated by the arrows in FIG. 3.

It is understood that additional embodiments herein may be realized by modifying some of the elements described above.

In one embodiment, the method is applied to identify the location of an arrhythmia source but not to ablate it. In this embodiment, none of the electrodes on the electrode array need to be configured to be able to deliver ablative energy to biological tissue.

In one embodiment, the depth of the arrhythmia source in the cardiovascular tissue is computed from the locations of the electrodes in the X-ray plane and the arrival times at the electrodes of the electrical impulse emanating from the arrhythmia source. This additional determination of depth of the arrhythmia within the cardiovascular tissue generally will require obtaining data from a greater number of electrodes. The depth of the source in the tissue is important clinically because it informs an operator of how deep a lesion will be required to ablate the arrhythmia source. Additionally, if the electrode array is located within the heart and the arrhythmia source is determined to be located near the epicardial surface the operator may choose to attempt the ablation from the epicardial side. Conversely, if the electrode array is placed on the epicardial surface and the arrhythmia source is determined to be located close to the endocardial surface the operator may choose to attempt the ablation from the endocardial surface.

In another embodiment, the one or more ablation electrodes are irrigated with an irrigation fluid delivered through a tube in the shaft of the catheter during the ablation procedure. The irrigation of the ablation electrode reduces the likelihood of tissue charring, occurrence of steam pops which may disrupt the tissue, and coagulation of blood. Coagulated blood may form emboli that travel through the vascular system and cause damage to remote tissues. Emboli lodging in the brain, for example, can cause strokes.

In another embodiment, the conduction velocity of the electrical impulse is not assumed to be constant in all directions but may be represented by a two-component spatial vector. It is known that conduction velocity varies with the orientation of cardiac fibers. Computing separately the two components of the conduction velocity may improve the accuracy of the computation of the location of the arrhythmia source. Since the ablation electrode is moved iteratively in a sequence of steps, a more accurate determination of the location of arrhythmia source in each step may shorten the overall time required to move the electrode within a specified threshold distance of the arrhythmia source. However, signals from a greater number of electrodes may be needed to accurately compute a two-component vector representation of the conduction velocity compared with computing a single scalar representation of the conduction velocity.

In another embodiment, the recordings obtained from the electrodes are processed to obtain other electrical measures in addition to the electrical measure of the arrival times of the electrical impulse emanating from the arrhythmia source. Such other measures may include electrical impedance of the electrodes or the amplitude of the electrical signal detected by the electrodes. In this embodiment, the location of the arrhythmia source is computed to be consistent with the measured locations of the electrodes and the one or more electrical measures. Damaged or scarred tissue is characterized by altered electrical impedance and that the amplitude of the electrical activity is diminished in regions of damaged or scarred tissue. Arrhythmia sources also tend to be located in regions of damaged or scarred tissue so that these additional measures may improve the determination of the location of the arrhythmia source.

In another embodiment, electroanatomic imaging is employed in addition to, or in replacement of, X-ray imaging.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth throughout do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method of determining a location of an arrhythmia source of a cardiac arrhythmia comprising:
   introducing into a body of a patient a catheter containing an array of electrodes;
   positioning the catheter such that a plurality of electrodes from the array of electrodes contact cardiovascular tissue in the body;
   obtaining an image of the array of electrodes in the body;
   measuring, in the image, locations of multiple electrodes in the array;
   constructing a computer simulated model of the array of electrodes;
   computing projected locations, in the image, of the electrodes in the computer simulated model;

computing a position and angular orientation of the computer simulated model which results in the projected locations, in the image, of the electrodes in the simulated model matching the measured locations, in the image, of the electrodes;

obtaining recordings of electrical activity from the cardiovascular tissue through the plurality of electrodes in contact with the cardiovascular tissue;

processing the recordings to obtain arrival times at the plurality of electrodes in contact with the cardiovascular tissue of an electrical impulse emanating from the arrhythmia source;

computing a location of the arrhythmia source based on the position and angular orientation of the simulated model and the arrival times; and based on the location of the arrhythmia source, performing a step comprising at least one of repositioning the catheter and delivering ablative energy through the catheter.

2. The method of claim 1, further comprising displaying the computed location of the arrhythmia source on a display.

3. The method of claim 1, wherein obtaining an image of the array of electrodes in the body comprises using X-ray or electroanatomic imaging.

4. The method of claim 1, wherein the catheter contains markers configured to identify, in the image, individual electrodes of the array of electrodes.

5. The method of claim 1, wherein the array of electrodes comprises a central electrode and a plurality of electrodes located on deployable wings surrounding the central electrode.

6. The method of claim 1, wherein the catheter includes a plurality of deployable wings, and each deployable wing includes one or more electrodes.

7. The method of claim 1, further comprising computing an orientation of a tissue plane of the cardiac tissue on which the plurality of electrodes in contact with the cardiac tissue rests.

8. The method of claim 7, wherein computing a location of the arrhythmia source based on the locations of the plurality of electrodes comprises computing the location of the arrhythmia source in the tissue plane.

9. The method of claim 1, further comprising computing a scalar or a two-dimensional vector representation of the conduction velocity of an electrical impulse emanating from the arrhythmia source.

10. The method of claim 1, further comprising computing a depth of the arrhythmia source within the cardiovascular tissue.

11. The method of claim 1, further comprising displaying the computed location of the arrhythmia source superimposed on the image.

12. The method of claim 1, wherein computing a position and angular orientation of a simulated model of the electrode array comprises determining a value of a projection scale factor.

13. A method of treating a cardiac arrhythmia comprising:
introducing into the body of a patient a catheter containing an array of electrodes, at least one of the array of electrodes being an ablation electrode configured to ablate biological tissue;

positioning the catheter such that at least a plurality of electrodes of the array of electrodes is in contact with cardiovascular tissue in the patient;

obtaining an image of the array of electrodes in the body;

measuring, in the image, locations of multiple electrodes in the array;

constructing a computer simulated model of the array of electrodes;

computing projected locations, in the image, of the electrodes in the computer simulated model;

computing a position and angular orientation of the computer simulated model which results in the projected locations, in the image, of the electrodes in the simulated model matching the measured locations, in the image, of the electrodes;

obtaining recordings of electrical activity from the cardiovascular tissue through the plurality of electrodes;

processing the recordings to obtain arrival times at the plurality of electrodes of an electrical impulse emanating from an arrhythmia source;

computing a location of the arrhythmia source based on the position and angular orientation of the simulated model and the arrival times;

repositioning the catheter such that the ablation electrode is adjacent to the computed location of the arrhythmia source; and ablating the arrhythmia source using the ablation electrode.

14. The method of claim 13, further comprising, when computing the location of the arrhythmia source, computing a distance of the ablation electrode to the arrhythmia source; and when repositioning the catheter, using a computed distance to position the ablation electrode adjacent to the arrhythmia source.

15. The method of claim 13, further comprising iterating the steps of:
obtaining an image, measuring, constructing, computing projected locations, computing a position and an angular orientation, obtaining recordings, processing the recordings, computing a location of the arrhythmia source, and repositioning the catheter until the computed distance of the ablation electrode to the arrhythmia source indicates that the ablation electrode is adjacent to the arrhythmia source.

16. The method of claim 13, further comprising irrigating the ablation electrode with fluid from an irrigation tube of the catheter.

17. The method of claim 13, wherein the arrhythmia source is ablated by delivering radiofrequency energy through the ablation electrode.

18. The method of claim 13, wherein the arrhythmia source is ablated by delivering energy configured to irreversibly electroporate biological tissue through the ablation electrode.

19. The method of claim 13, further comprising displaying the computed location of the arrhythmia source superimposed on the image.

20. The method of claim 13, wherein computing a position and angular orientation of a simulated model of the electrode array comprises determining a value of a projection scale factor.

21. A method of determining the location of an arrhythmia source of a cardiac arrhythmia comprising:
introducing into the body of a patient a catheter containing an array of electrodes;

positioning the catheter so that a plurality of electrodes in the array of electrodes is in contact with cardiovascular tissue of the patient;

obtaining an image of the array of electrodes in the body;
measuring, in the image, locations of multiple electrodes in the array;
constructing a computer simulated model of the array of electrodes;
computing projected locations, in the image, of the electrodes in the computer simulated model;
computing a position and angular orientation of the computer simulated model which results in the projected locations, in the image, of the electrodes in the simulated model matching the measured locations, in the image, of the electrodes;
obtaining recordings of electrical activity from the cardiovascular tissue through the plurality of electrodes in contact with the cardiovascular tissue;
processing the recordings to obtain one or more electrical measures of the recordings;
computing a location of the arrhythmia source based on the position and angular orientation of the simulated model and the one or more electrical measures; and
based on the location of the arrhythmia source, performing a step comprising at least one of repositioning the catheter and delivering ablative energy through the catheter.

22. The method of claim 21, wherein the electrical measures of the recordings are at least one of arrival times at the plurality of electrodes of the electrical impulse emanating from the arrhythmia source, electrical impedances, and amplitudes of electrical signals.

23. The method of claim 21, further comprising displaying the computed location of the arrhythmia source on a display.

24. The method of claim 21, further comprising displaying the computed location of the arrhythmia source superimposed on the image.

25. The method of claim 21, wherein computing a position and angular orientation of a simulated model of the electrode array comprises determining a value of a projection scale factor.

* * * * *